US006579672B1

(12) United States Patent
Granger et al.

(10) Patent No.: US 6,579,672 B1
(45) Date of Patent: *Jun. 17, 2003

(54) SPECIMEN COLLECTION FLUID

(75) Inventors: Vivian Granger, Sheffield (GB); David Barnett, Sheffield (GB)

(73) Assignees: Northern General Hospital, Sheffield (GB); Central Sheffield University Hospitals NHS Trust Royal Hallamshire Hospital, Sheffield (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/194,333

(22) PCT Filed: May 23, 1997

(86) PCT No.: PCT/GB97/01418

§ 371 (c)(1),
(2), (4) Date: Apr. 26, 1999

(87) PCT Pub. No.: WO97/45729

PCT Pub. Date: Dec. 4, 1997

(30) Foreign Application Priority Data

May 24, 1996 (GB) .............................................. 9611000

(51) Int. Cl.⁷ .................................................. A01N 1/02
(52) U.S. Cl. ............................................. 435/2; 436/10
(58) Field of Search ................................ 435/2; 436/10

(56) References Cited

U.S. PATENT DOCUMENTS 4,302,355 A 11/1981 Turner, Jr. et al. .......... 252/408
5,538,894 A 7/1996 Patscheke et al. ............ 436/18
5,858,699 A * 1/1999 Granger et al. .......... 435/40.51

FOREIGN PATENT DOCUMENTS

| EP | 0 642 022 A | 3/1995 | |
| FR | 2 331 352 A | 6/1977 | |
| GB | 2 001 757 A | 2/1979 | |
| GB | 1 563 839 | 4/1980 | .......... G01N/33/48 |
| JP | 60 006865 A | 1/1985 | |
| WO | WO 95/01796 | 1/1995 | .......... A61K/35/14 |
| WO | WO 95/27203 | 10/1995 | .......... G01N/33/50 |

OTHER PUBLICATIONS

Merck Index, 11th Edition, 1989, entry 6975, p. 1112.*

Van Holde, K.E. "Physical Biochemistry", 1971, Prentice Hall, p. 43.*

Barnett et al., "Evaluation of a novel whole blood quality control material for lymphocyte subset analysis: results from the UK NEQAS immune monitoing scheme", Cytometry, vol. 26, No. 3, Sep. 15, 1996, pp. 216–222.

* cited by examiner

*Primary Examiner*—Irene Marx
(74) *Attorney, Agent, or Firm*—Fish & Richardson P.C.

(57) ABSTRACT

A sterile aqueous specimen collection fluid containing a buffer, an aliphatic aldehyde at a concentration of 0.15M to 3.4M, and one or more heavy metal salts at a concentration of $0.2 \times 10^{-3}$M to 0.2M, and having a pH of 6.8 to 8.0. Also disclosed is a method of colleting a specimen with such a fluid for haematological analysis.

3 Claims, 20 Drawing Sheets

FIG. 1

LeucoGATE [1]

14:45M1904001

Gate: FSC  SSC
       64   51
      255   51
      255    0
       64    0

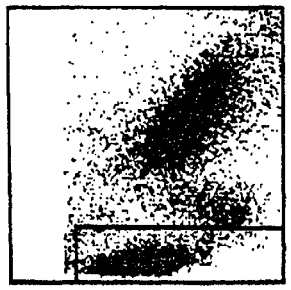
FSC

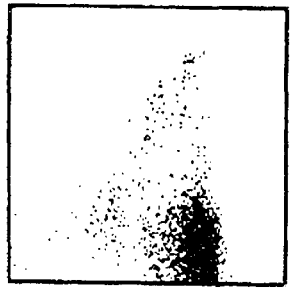
HLe-1

Mean: 124  20    Gated Events: 4705        Quadrant correction: Yes
                 Total Events: 15000

| Gate Description: | %Lymphs | %Monos | %Grans | %Debris | %Lymphs of total |
|---|---|---|---|---|---|
| | 97 | 1 | 2 | 1 | 98 |

White cell count: 6.1 (x $10^3$ cells/cu mm)   %Lymphs: 31.0

| Three Part Differential | % of Leucocytes | cells/cu mm |
|---|---|---|
| Lymphocytes | 31 | 1890 |
| Monocytes | 7 | 430 |
| Granulocytes | 62 | 3780 |

Control      [1]

14:45M1904002

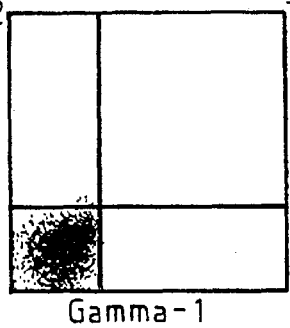

Markers:
FL1  84
FL2  76

Gamma-1

| Quad | Cell Type | Corr %L | Cells cu mm |
|---|---|---|---|
| 1 | NSS PE | 0 | 0 |
| 2 | NSS++ | 0 | 0 |
| 3 | Unstained | 100 | 1890 |
| 4 | NSS FITC | 0 | 0 |

FSC Mean: 124    Gated Events: 2582
SSC Mean:  20    Total Events: 8000

FIG. 3

LeucoGATE [1]

14: CONT190001

Gate: FSC SSC
70 58
175 58
175 0
70 0

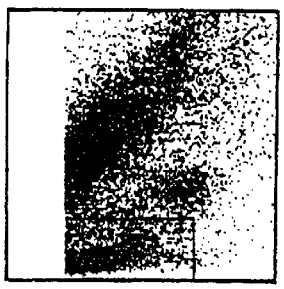
FSC

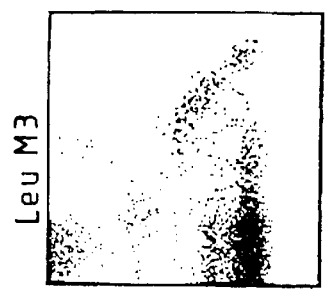
HLe-1

Mean: 99 26   Gated Events: 3477   Quadrant correction: Yes
Total Events: 15000

| Gate Description: | %Lymphs | %Monos | %Grans | %Debris | %Lymphs of total |
|---|---|---|---|---|---|
| | 80 | 2 | 11* | 7 | 97 |

White cell count: 6.1 (x $10^3$ cells/cu mm)   %Lymphs: 22.0

| Three Part Differential | % of Leucocytes | cells/cu mm |
|---|---|---|
| Lymphocytes | 22 | 1340 |
| Monocytes | 9 | 550 |
| Granulocytes | 70 | 4270 |

Control  [1]

14: CONT190002

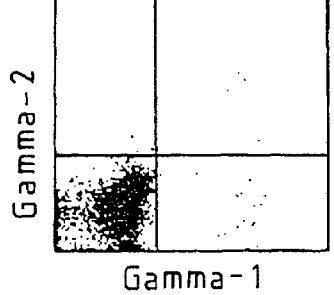

Markers:
FL1 92
FL2 88

Gamma-1

FSC Mean: 100   Gated Events: 2728
SSC Mean: 25    Total Events: 12000

| Quad | Cell Type | Corr %L | Cells cu mm |
|---|---|---|---|
| 1 | NSS PE | 0 | 0 |
| 2 | NSS++ | 0 | 0 |
| 3 | Unstained | 99 | 1330 |
| 4 | NSS FITC | 1 | 10 | cd3/cd19 [1]

14:CONT190003

| Quad | Cell Type | Corr %L | Cells/ cu mm |
|------|-----------|---------|--------------|
| 1 | CD3-/CD19+ | 28 | 380 |
| 2 | CD3+/CD19+ | 3 | 40 |
| 3 | CD3-/CD19- | 8 | 110 |
| 4 | CD3+/CD19- | 60 | 800 |

| Subset Label | Corr %L |
|--------------|---------|
| Q1 CD3/CD19 | 28 ok |
| Q2 CD3/CD19 | 3 ok |
| Q3 CD3/CD19 | 8 ok |
| Q4 CD3/CD19 | 60 ok |

Markers:
FL1 92
FL2 88

FSC Mean: 101  Gated Events: 2544
SSC Mean: 25   Total Events: 1200

>> Results for this Simultest are suspect due to non-lymphs in gate. <<

For research use only. Not for use in diagnostic or therapeutic procedures.

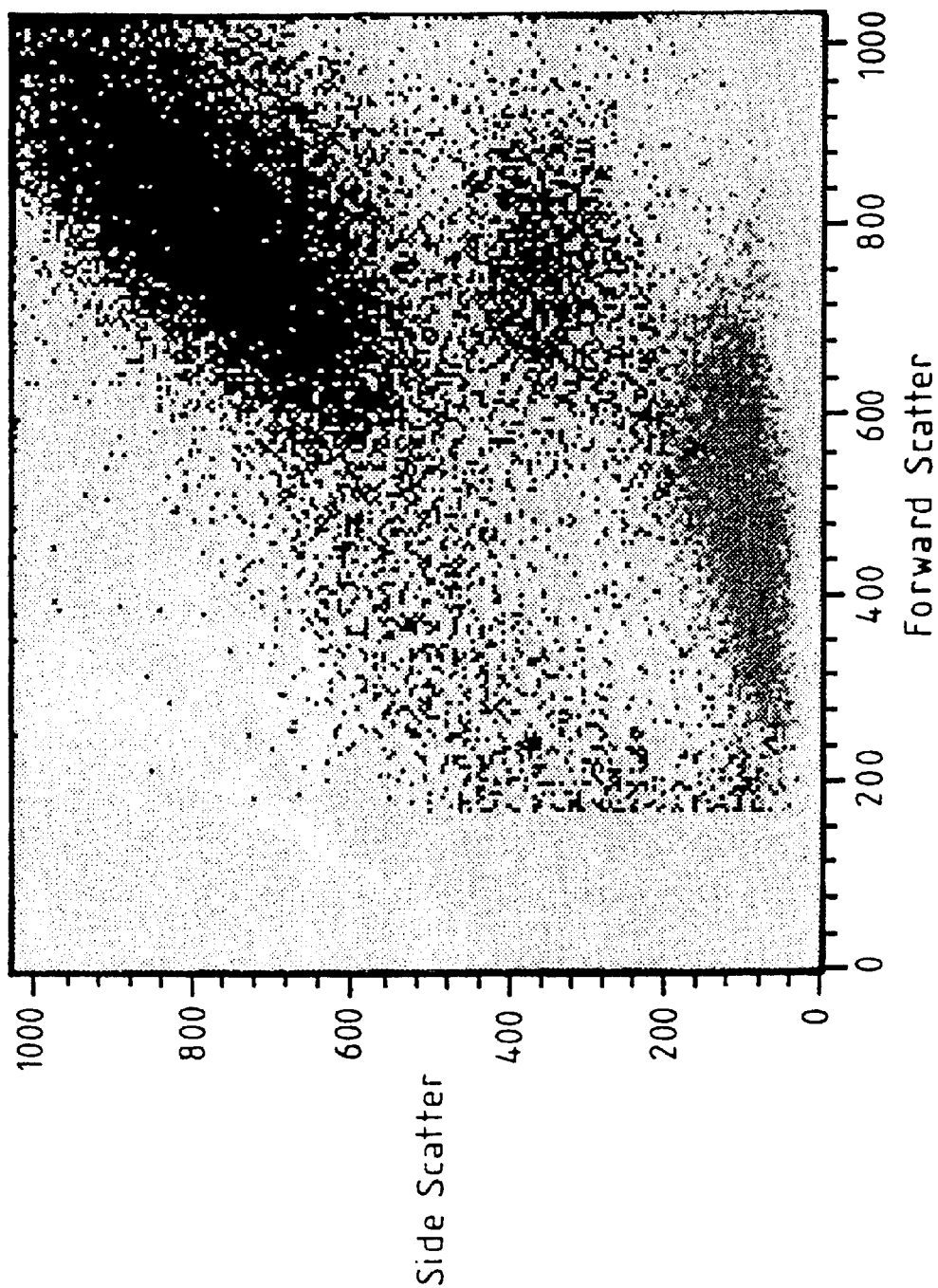

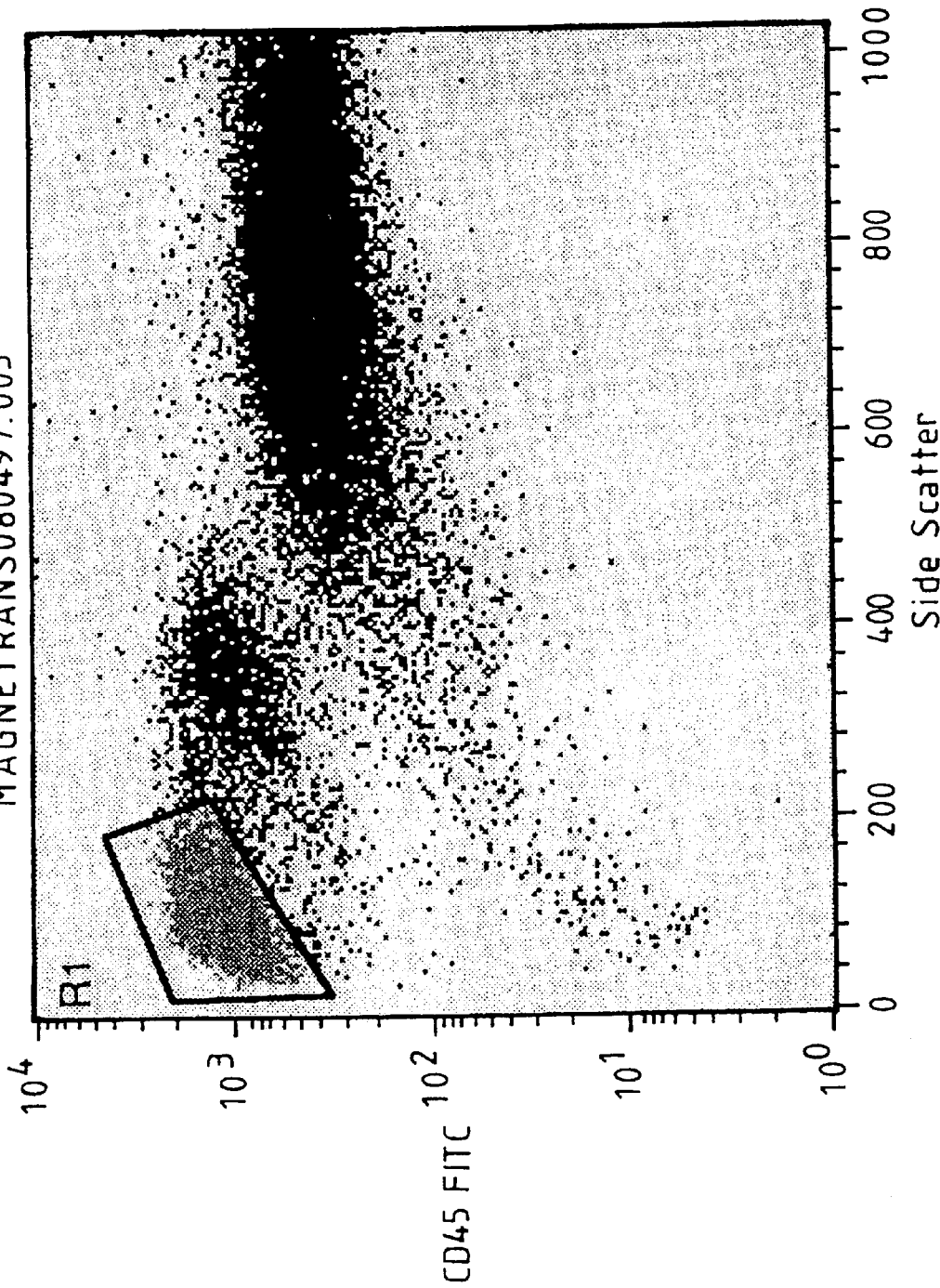

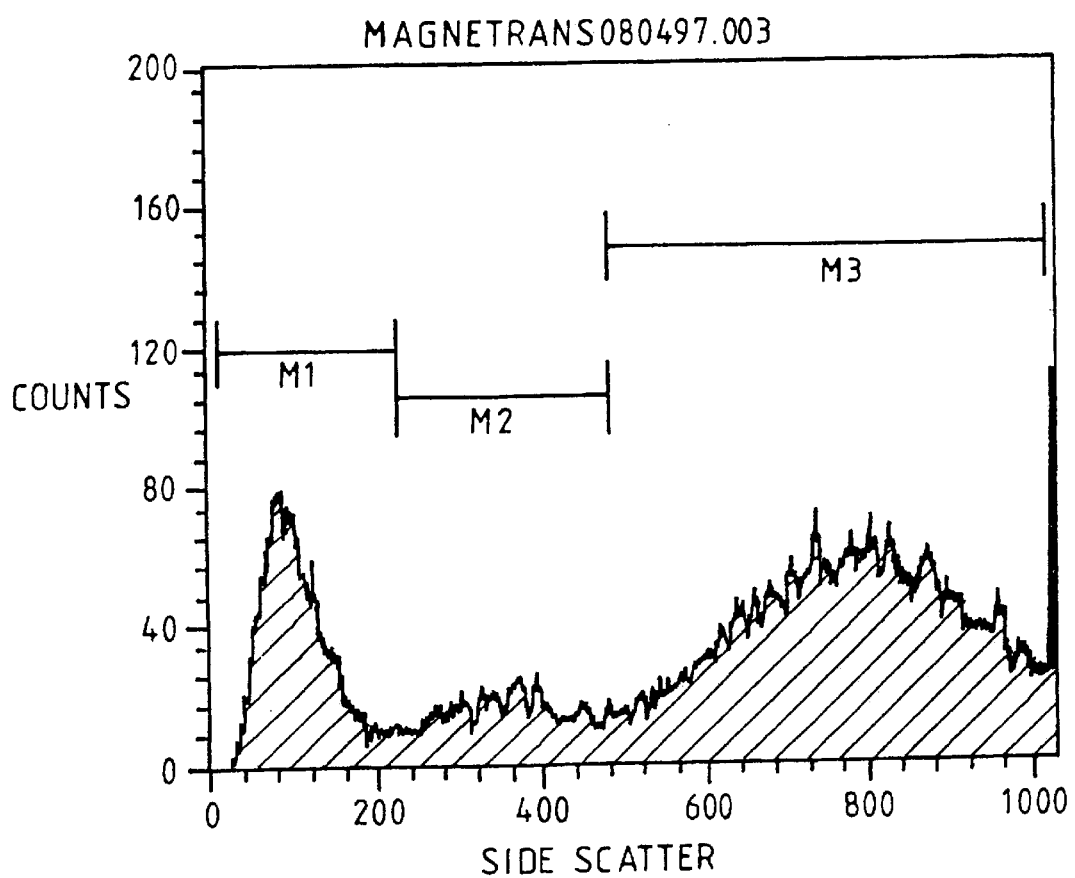

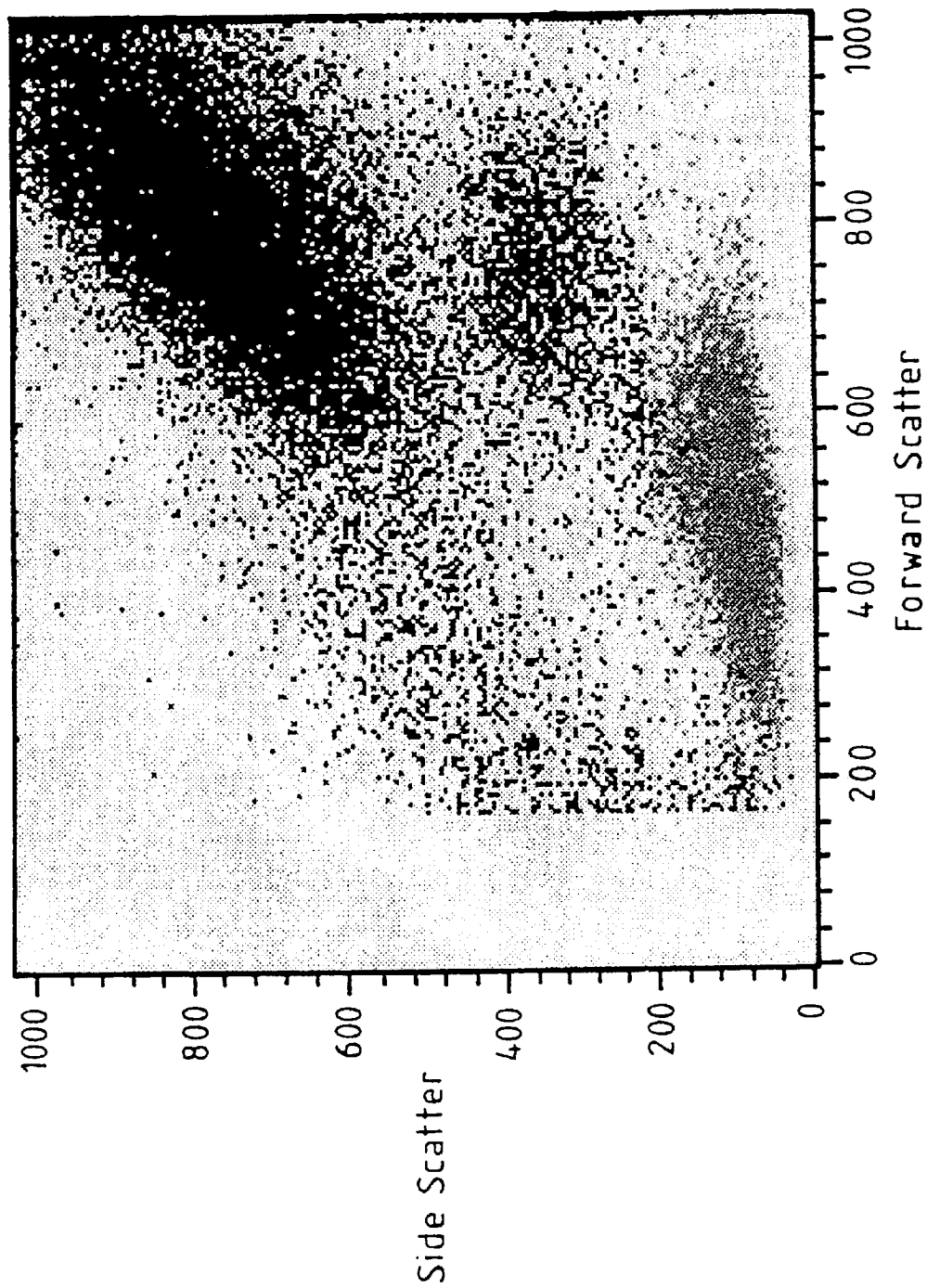

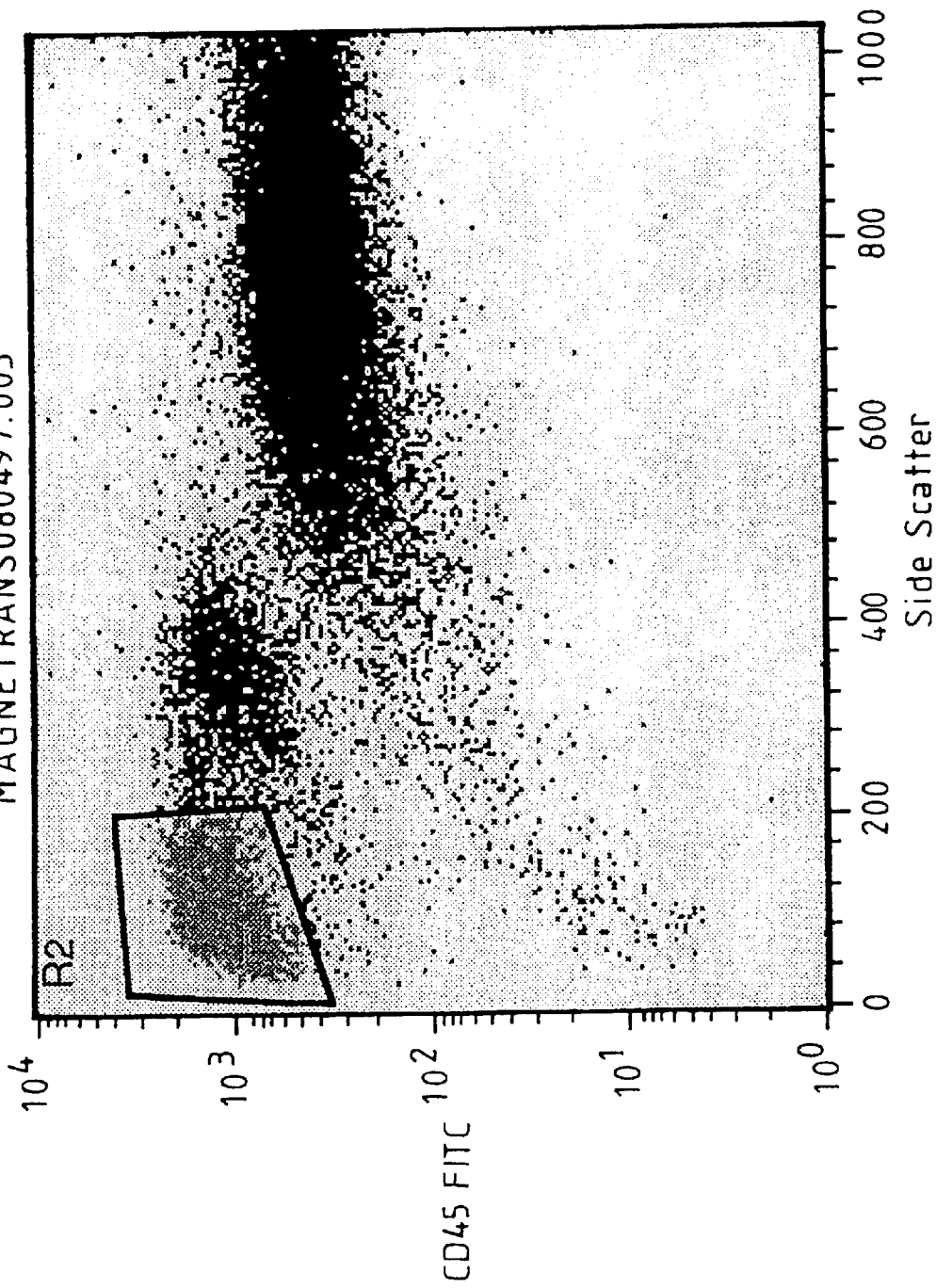

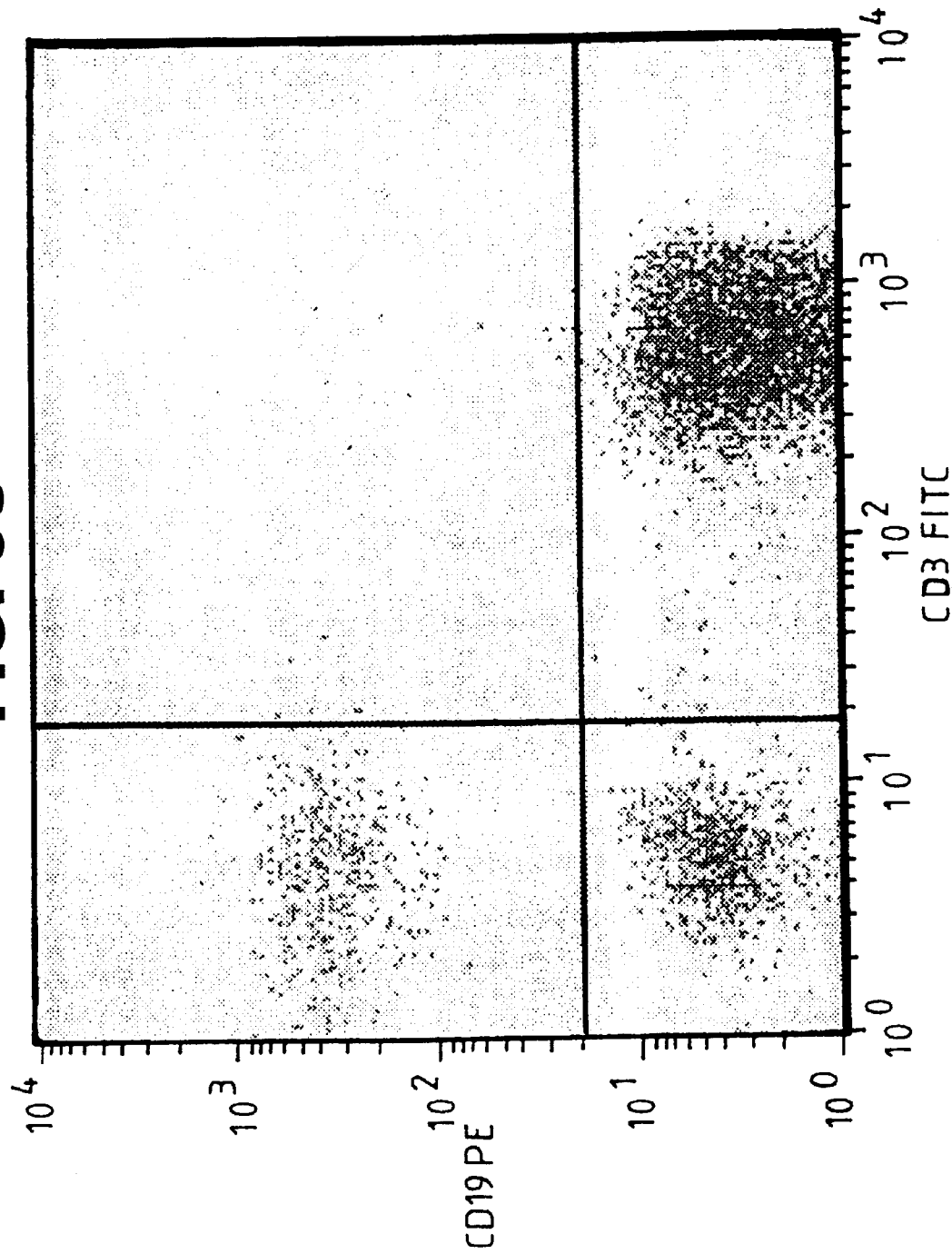

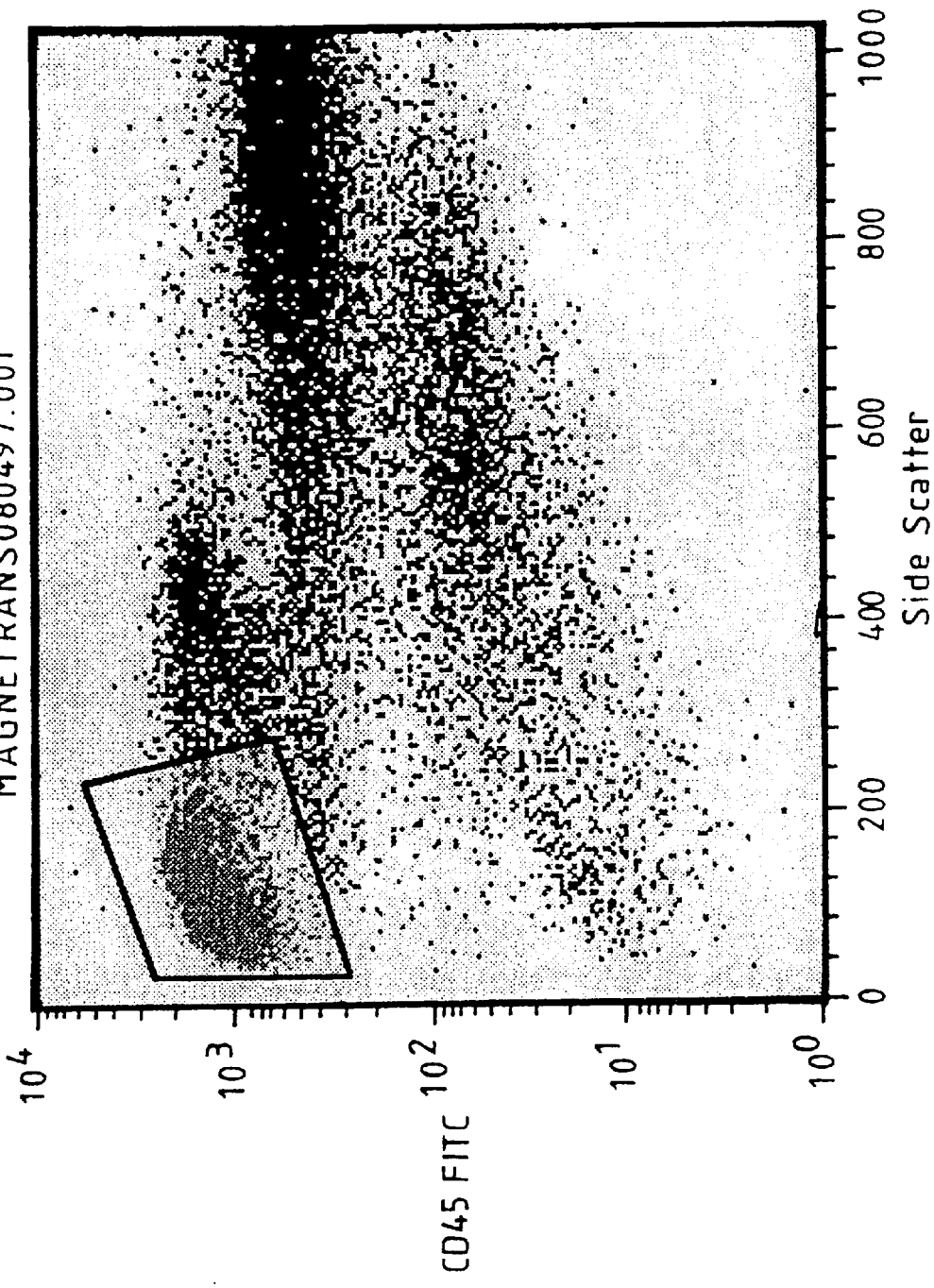

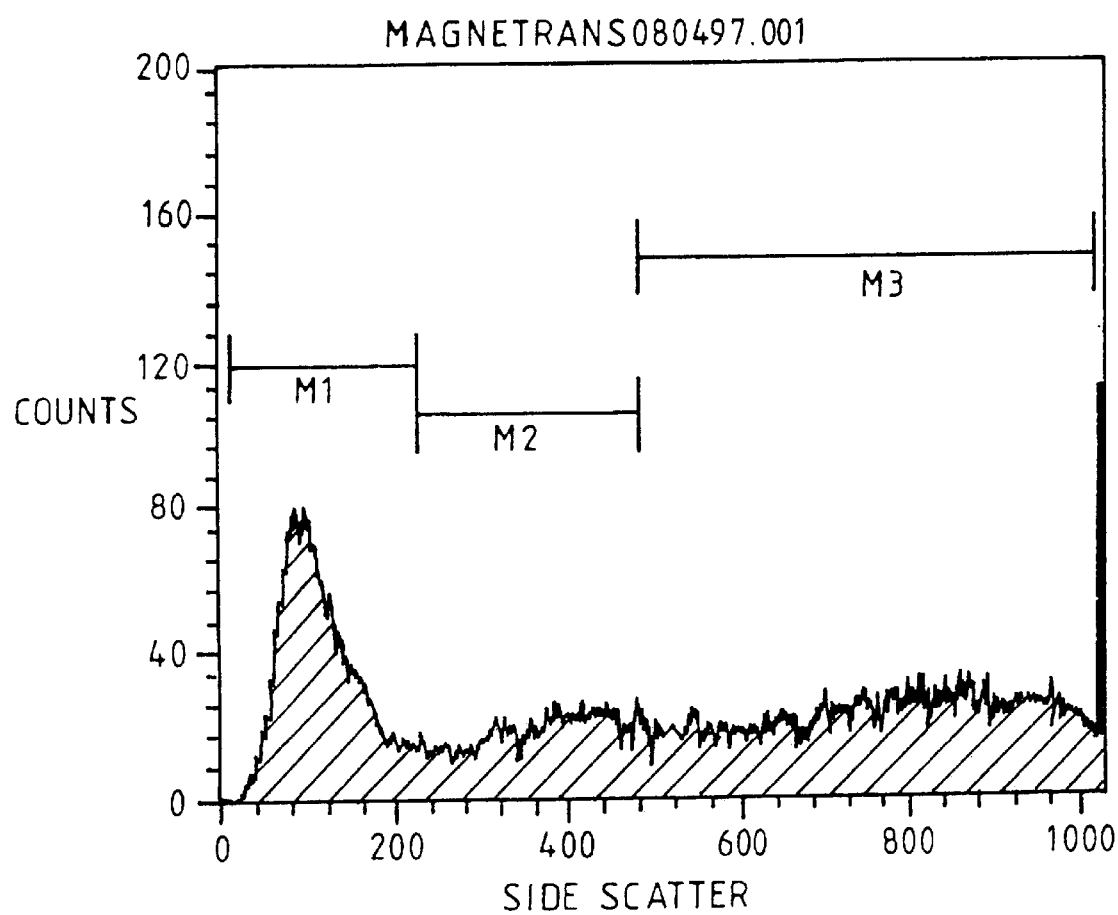

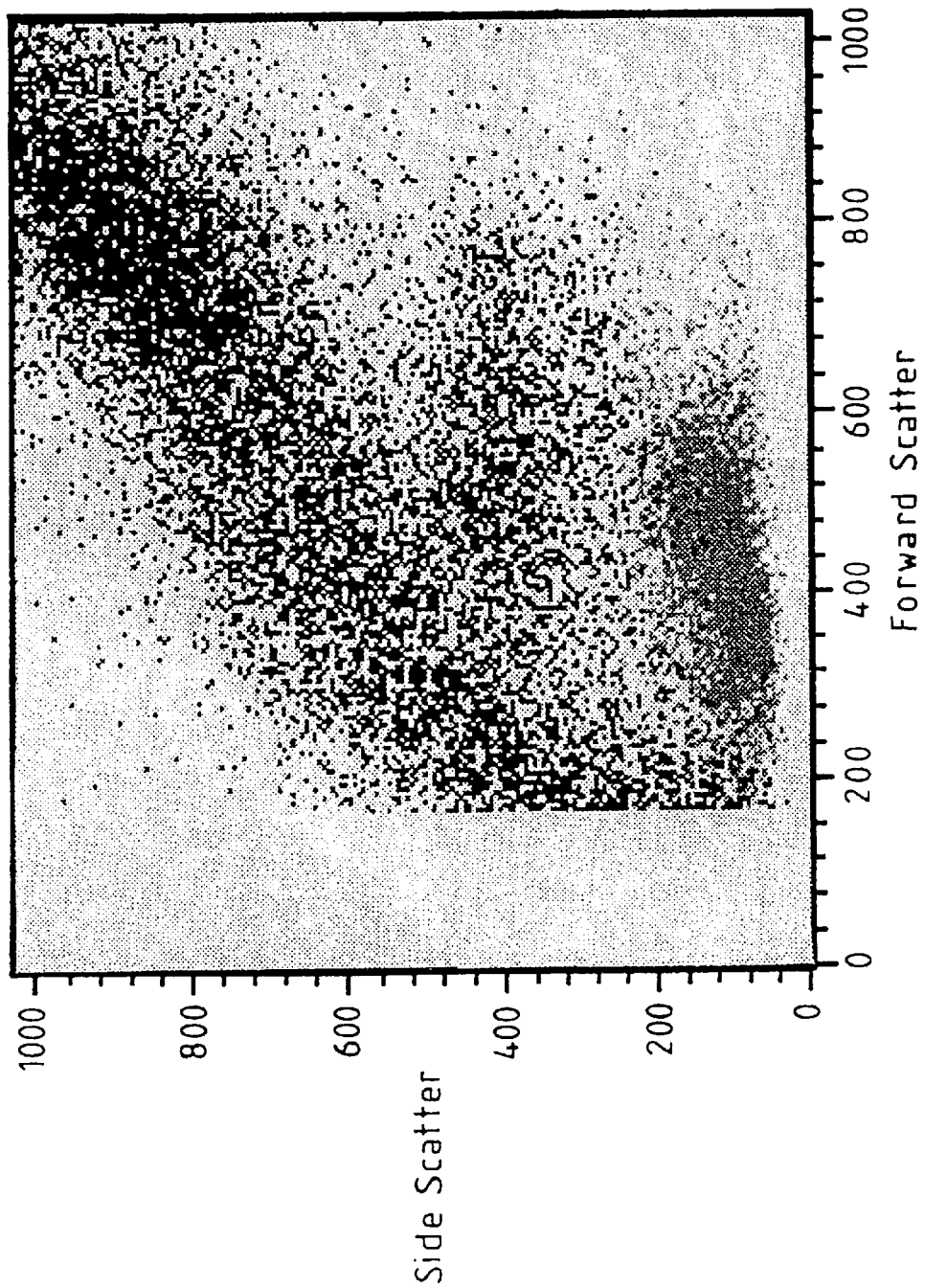

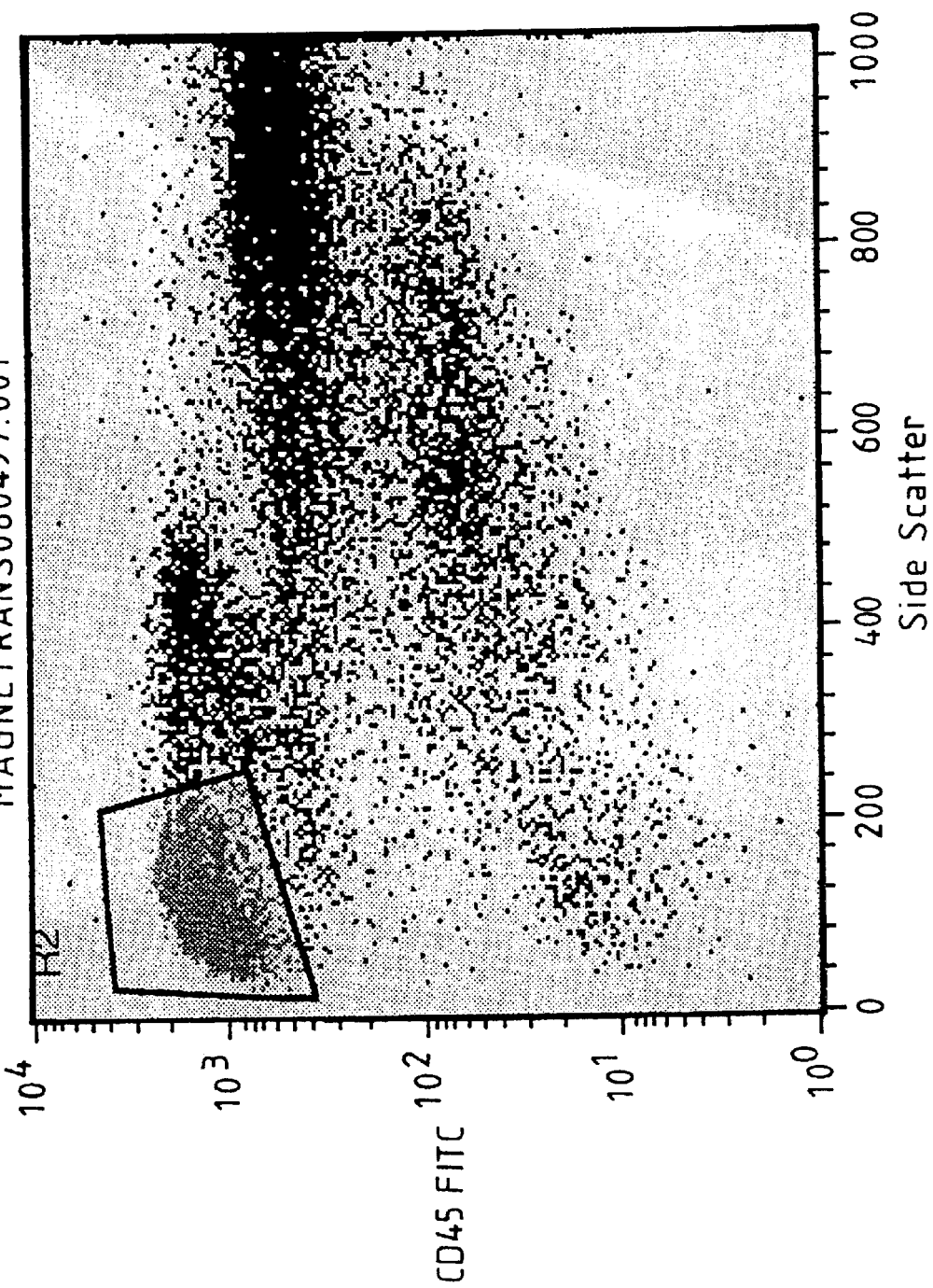

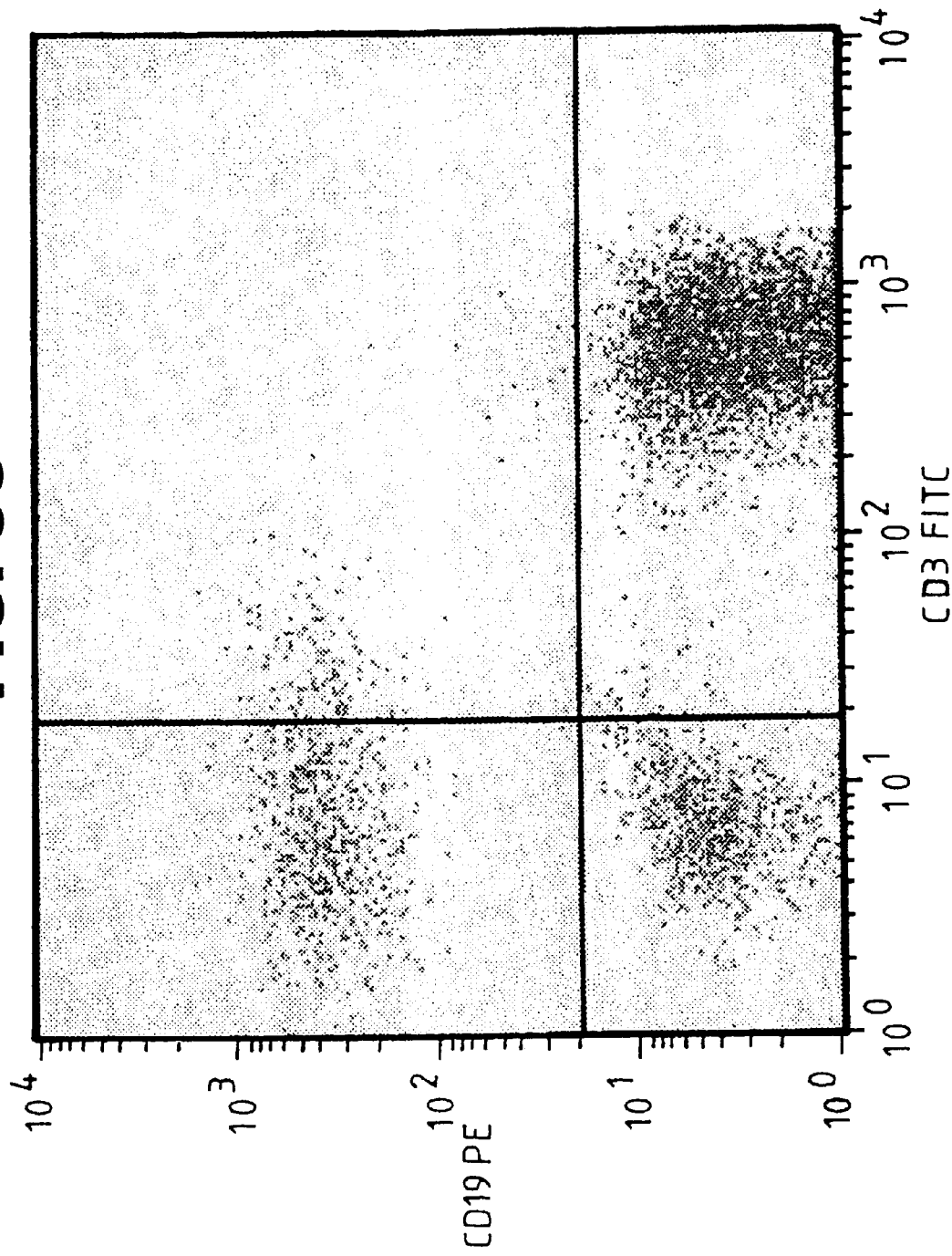

Full Blood Count profile of a stabilised specimen 3 days post venepuncture.
( Coulter STKS analyser profile )

```
04/07/97    13:30:12
            BET
```

| ID# 1  997 | WBC | 7.5 |     | RBC  | 4.77  |
|---|---|---|---|---|---|
| ID# 2      |     | %   | #   | HGB  | 14.3  |
| Sequence # | NE  | 63.0 | 4.7 | HCT | 0.430 |
|            | LY  | 24.2 | 1.8 | MCV | 90.1  |
| DATE:  04/07/97 | MO | 9.6 | 0.7 | MCH | 30.1 |
| TIME:  13:30:05 | EO | 2.5 | 0.2 | MCHC | 33.4 |
| <u>cassette</u>   S | BA | 0.7 | 0.1 | RDW | 12.9 |

Normal WBC Pop
Normal RBC Pop
Abnormal PLT Pop

PLT   167
MPV   12.0   H
PCT   0.201
PDW   18.5

SUSPECT  FLAGS:

--------WBC----------------RBC--------------PLT--------
DEFINITIVE  FLAGS:
                         Large Platelets

FIG. 10A

TABLE 1

Absolute values for White Cell differential over a 5 day period.
Results expressed as x10⁹/l

| | DAY 0 | DAY 3 | DAY 4 | DAY 5 |
|---|---|---|---|---|
| Granulocytes | 4.8 | 4.7 | 4.6 | 5.0 |
| Lymphocytes | 1.7 | 1.8 | 1.8 | 1.8 |
| Monocytes | 0.7 | 0.7 | 0.9 | 0.8 |
| Eosinophils | 0.2 | 0.2 | 0.3 | 0.3 |

TABLE 2

Percentage values for White Cell differential over a 5 day period.

| | DAY 0 | DAY 3 | DAY 4 | DAY 5 |
|---|---|---|---|---|
| Granulocytes | 66.1 | 63.0 | 60.7 | 63.3 |
| Lymphocytes | 22.4 | 24.2 | 24.1 | 23.4 |
| Monocytes | 8.8 | 9.6 | 11.7 | 9.5 |
| Eosinophils | 2.6 | 2.5 | 3.5 | 3.8 |

SPECIMEN COLLECTION FLUID

BACKGROUND OF THE INVENTION

This invention relates to specimen collection fluids, and more particularly to a specimen collection fluid for the treatment of blood and/or bone marrow specimens to be used for immunohaematological analysis.

The current methods of immunohaematological analysis of specimens obtained from patients suffering from haematological malignancies and immunological disorders such as AIDS require the specimen to be collected into a sterile blood collection tube containing an appropriate amount of a specimen collection fluid, which is usually an anticoagulant solution. However, several studies have reported that collection of peripheral blood or bone marrow requires that such specimens should be processed within a 6, 18 or 24 hour period, depending on the test involved, to ensure antigen stability and no deterioration of sample integrity. Due to these strict time limitations, the transportation of a specimen to the analysis site is almost always required to be carried out on a very urgent basis. If analysis is delayed, for example, if a patient's specimen is obtained on a weekend or a bank holiday, or a specimen is transported from one country to another, it may not be in a suitable condition when finally submitted to analysis, and a further specimen may need to be taken.

Stabilisation fluids presently available require the collection of anticoagulated blood and then the addition of 1 ml of specimen collection fluid to 1 ml of the anticoagulated blood specimen, resulting in a considerable dilution of the specimen, which makes the results of the subsequent immunohaematological analysis very difficult to interpret.

By a "specimen collection fluid" in this specification is meant a fluid which is mixed, in use, with a specimen to be analyzed to provide the specimen with improved storage properties and which remains in contact with the specimen during storage without substantially interfering with the subsequent analysis.

Commercially available stabilisation fluids also give poor results with leukemics.

In international patent applications nos WO 95/01796 and WO 95/27203 there are described stabilised cell preparations prepared by treating the cells with a stabilising agent comprising a heavy metal compound, particularly a transition metal salt. The stabilising agent may also comprise an effective amount of an aldehyde. The stabilised cell preparations can be stabilised whole blood preparations for use in quality control procedures for analytical techniques.

OBJECTS OF THE INVENTION

It is an object of the invention to provide an improved specimen collection stabilisation fluid suitable for imunohaematological analysis specimens, which in preferred embodiments, can allow the collection of a specimen directly into a specimen collection container containing the stabilisation fluid.

It is also an object of the invention to provide a specimen collection container comprising an improved specimen collection fluid.

It is a further object of the invention to provide a method of collection of specimens, for example, for immunohaematological analysis, which comprises contacting the specimens with a novel specimen collection fluid providing improved storage properties without substantially interfering with the analysis.

SUMMARY OF THE INVENTION

In a first aspect the invention provides a specimen collection fluid, for example, for immunohaematological analysis specimens, which comprises a sterile buffered aqueous solution comprising an aliphatic aldehyde, at a molar concentration of 0.15M to 3.4M, one or more heavy metal salts, at a total molar concentration of $0.2 \times 10^{-3}$M to 0.2M, and, preferably, an anticoagulant, at a molar concentration of 0.27M to 0.45M, the solution having a pH in the range of 6.8 to 8.0.

It will be understood that in the case where blood already in an anticoagulated state is to be used, an anticoagulant is optional.

In another aspect the invention provides a specimen collection container for the reception of specimens for analysis, which contains a stabilising amount of a specimen collection fluid comprising a sterile aqueous solution comprising an aliphatic aldehyde, at a molar concentration of 0.15M to 3.4 M, one or more heavy metal salts, at a total molar concentration of $0.2 \times 10^{-3}$M to 0.2M, and an anticoagulant, at a molar concentration of 0.27M to 0.45M, the solution having a pH in the range of 6.8 to 8.0.

In a further aspect the invention provides a method of collection of specimens for immunohaematological analysis and/or other analytical techniques, for example such as histopathological analysis, which comprises contacting the specimen with a specimen collection fluid comprising a sterile aqueous solution comprising an aliphatic aldehyde, at a molar concentration of 0.15M to 3.4M, one or more heavy metal salts, at a total molar concentration of $0.2 \times 10^{-3}$M to 0.2M, and an anticoagulant, at a molar concentration of 0.27M to 0.45M, the solution having a pH in the range of from 6.8 to 8.0.

BRIEF DESCRIPTION OF THE FIGURES

FIGS. 1 and 2 are the results from forward and side scatter (FSC) for a blood sample stored in contact with a specimen collection fluid of this invention.

FIGS. 3 and 4 are the results from an unstabilized control.

FIGS. 5 and 6 are the results from CD45+staining, forward and side scatter for a blood sample stored in contact with a specimen collection fluid of this invention.

FIGS. 7 and 8 are the results from an unstabilized control.

FIG. 10 show in tables 1 and 2, respectively, absolute values and percentage values for white cell differential over a five-day period measured on a blood specimen stored in contact with a specimen collection fluid of this invention.

DETAILED DESCRIPTION OF THE INVENTION

Figure 2:
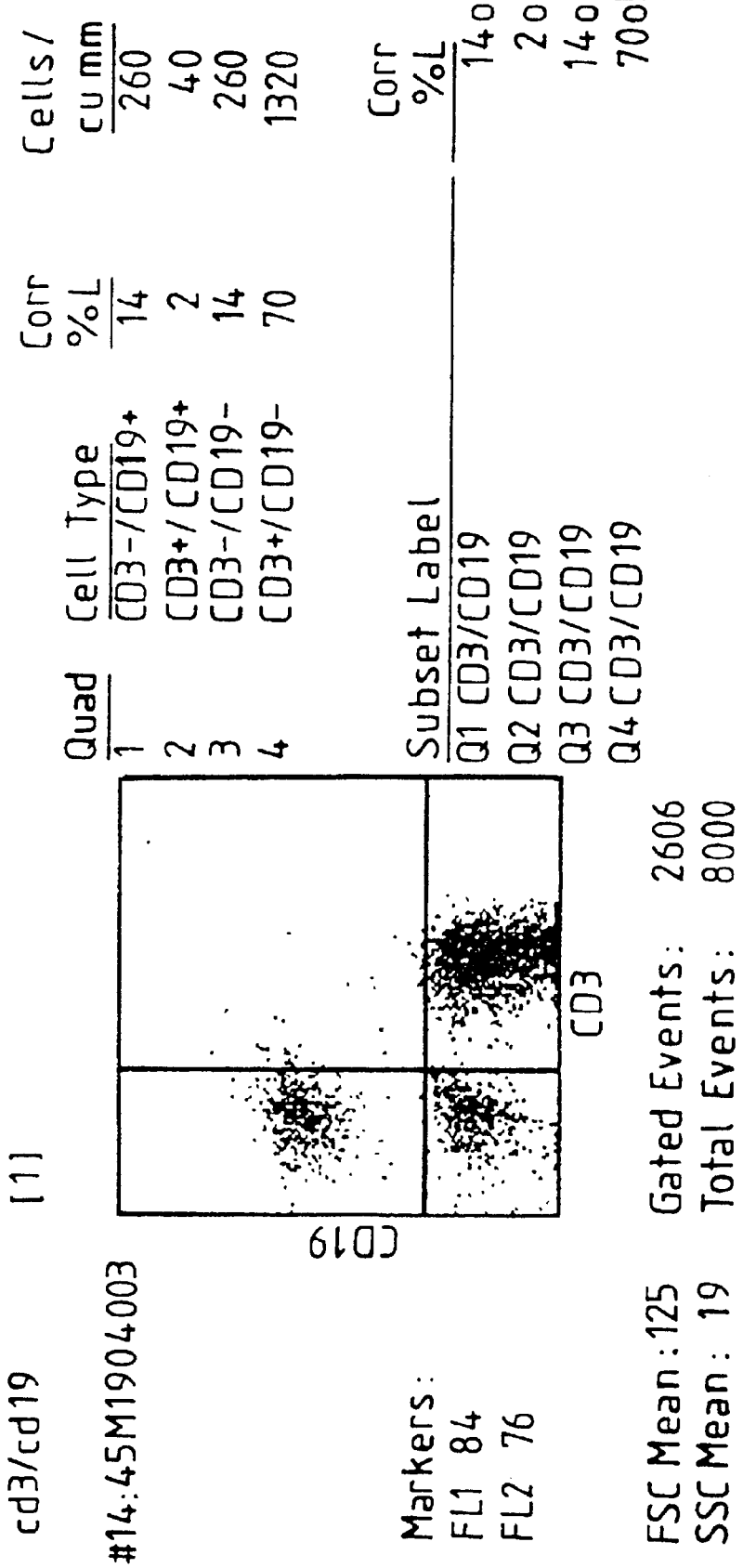

The invention is particularly applicable to the collection of peripheral blood and bone marrow specimens for immunohaematological analysis purposes, and will be henceforth more particularly described with reference thereto. It is to be understood, however, that the invention is not limited to the collection of such materials and is broadly applicable to a wide range of human and animal specimens collected for analytical purposes, such as analysis of pathological specimens, for example, histopathology.

The aliphatic aldehyde used in the specimen collection fluid can be any suitable aliphatic aldehyde, but is preferably formaldehyde, and most preferably paraformaldehyde. To assist in dissolving the aldehyde in the aqueous solution the solution can be warmed if necessary, but the temperature should not be allowed to rise above 50° C.

Suitable heavy metal salts are those of metals having complexing properties and having an atomic weight greater than 20, for example, transition metals, particularly transition metals of groups IVA to VIIA of the Periodic Table, for example, manganese, chromium, molybdenum, vanadium and titanium, group IB, for example, copper, and group IVB, for example, tin. Group VIA and group VIIA, transition metals, and especially chromium and manganese, are particularly preferred. Very good results have been obtained using manganese salts which have the advantage for some purposes that they have colourless solutions, and especially, mixtures of manganese and chromium salts.

Any suitable water soluble salts of such heavy metals may be used, especially inorganic acid salts, for example, sulphates, and particularly, chlorides. Particularly good results have been obtained using chromium and manganese compounds, for example, chromium salts such as chromic chloride $CrCl_3$, and manganese salts such as manganese chloride $MnCl_2$, and these are the preferred metal salts for use in the present invention.

Any suitable anticoagulant can be used, although EDTA salts are preferred, for example, alkali metal salts, such as, di-potassium ethylenediaminetetraacetic acid ($K_2EDTA$) and tri-potassium ethylenediaminetetraacetic acid ($K_3EDTA$). other anticoagulants which can be used include citrate/phosphate/dextrose/adenine (CPDA).

Preferred specimen collection fluids in accordance with the invention comprise aqueous solutions of paraformaldehyde, manganese and chromium chloride, and an anticoagulant. Preferably, the weight ratio of manganese to chromium is in the range of from 100:1 to 50:1, for example about 75:1.

The aqueous solution preferably comprises from 0.15 moles to 1.0 moles of the aliphatic aldehyde, from $0.2 \times 10^{-3}$M to 0.1 moles of the heavy metal salts, and from 0.27 to 0.45 moles of the anticoagulant. The aqueous solution preferably has a pH in the range of 7.2 to 7.6, for example, about 7.4.

The specimen collection fluid preferably also comprises one or more cell nutrients, for example, dextrose, adenosine tri-phosphate and inosine, and in amounts of respectively up to about 2.5M, 0.05M and 0.1M, and glycolitic pathway precursors, for example, di-hydroxy acetone and 2,3-diphosphoglycerol. Tri-sodium citrate and sodium chloride are, however, preferably omitted.

The specimen collection fluid preferably also comprises one or more antibiotics, to prevent bacterial growth which may otherwise occur, especially with nutrients present. Antibiotics, for example, chloramphenicol and neomycin sulphate, have been found to be suitable, in amounts of up to about 0.015M and 0.005M respectively.

The specimen collection fluid preferably also comprises a platelet stabiliser, for example magnesium chloride or iodoacetamide or its derivatives.

The specimen collection fluid can be used freshly made, or, if preferred, can be allowed to stand before use. It has been observed with some solutions of chromium compounds that the freshly made solutions give rise to the formation of a precipitate which it is believed may be a chromium hydroxy polymeric species. The precipitate is preferably filtered off from the solution before use. The formation of the precipitate will, of course, lower the concentration of heavy metal ions in the solution, and if this should occur, an analysis of the solution should be carried out to determine whether the concentration of the heavy metal salt is still within the preferred range.

The specimen collection container can, for example, be any suitable glass or plastics container of the type used in conventional blood collection systems for the collection of peripheral blood or bone marrow. The container can, for example, comprise a glass or plastic tube of capacity from 1 to 10 ml, preferably about 5 ml, excluding any air space, which has been rendered sterile by irradiation. Typically the specimen collection container will have a volume capable of containing at least ten micro-litres, and preferably 20 to 100 micro-litres, of specimen collection fluid, for example, about 50 microlitres.

In the collection method of the invention, blood or bone marrow may be drawn by any of the methods currently employed in the art of venesection directly into the specimen collection container. In general, aliquots of 5 ml of blood or bone marrow are suitable for most analytical purposes, and these can be drawn into the specimen collection container of the invention which may contain, for example, about 50 micro-litres of the novel specimen collection fluid.

The ratio of the volume of the specimen to the volume of the specimen collection fluid is preferably from 30:1 to 125:1.

By use of preferred embodiments of the specimen collection fluid, container and method of the invention, it has been found that immunohaematological analysis can be performed upon peripheral blood after more than 5 days and up to 7 days following collection without substantial deterioration in the antigen or cellular integrity. With preferred specimen collection fluids and methods of the invention it has been found that the leucocyte and platelet antigens CD3, CD4, CD5, CD8, CD10, CD13, CD16, CD14, CD19, CD20, CD33, CD34, HLA-DR, and CD45, and also the haematological parameters normally measured, for example, white cell count, red cell count, platelet count, white cell differential and haemoglobin, can remain substantially stable during this period. Because the white cell count remains substantially constant throughout, this assists in the determination of absolute values for antigens such as CD4 and CD34. RNA can be extracted from specimens for up to 5 days after collection, for example, for PCR analytical techniques.

The specimen collection fluid, container and method of the invention offer significant benefits in the management of disorders such as AIDS. The peripheral blood parameters remain substantially stable, facilitating the transportation of specimens over long distances or allowing retention of specimens until times which are convenient for analysis. The addition of small amounts of the specimen collection fluid, usually around one in 100 parts, does not introduce a significant dilution factor which will affect the absolute value calculations.

The invention is illustrated by the following Examples:

EXAMPLE 1

A specimen collection fluid is made up comprising a sterile aqueous solution containing the following components by weight:

| | |
|---|---|
| paraformaldehyde | 1.5 Molar |
| manganese chloride | 0.125 Molar |
| $K_2$EDTA | 0.37 Molar |

The pH of the solution is adjusted to 7.4 and the solution filtered. 50 μl of the solution is placed in a 7 ml glass specimen collection tube. A 24-hour-old blood sample which had been collected from a healthy donor into CPDA is taken and 5 ml drawn off into the tube. The contents of the tube are thoroughly mixed. The tube is preferably stored at 4° C. and the contents allowed to warm up to room temperature before testing.

Figure 4:
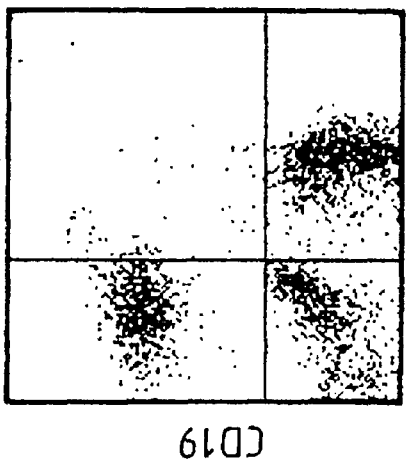

The specimen is tested on a Becton Dickinson flow cytometer after 5 days and compared with a similar unstabilised control. The results for forward and side scatter (FSC) are shown in FIGS. 1 and 2 (stabilised specimen) and FIGS. 3 and 4 (control). It can be seen that, whilst the stabilised specimen is comparatively unaffected, the non-lymphocytes and debris have built up in the control specimen to the extent that the measurements are regarded as unreliable.

Whilst in the above Example the specimen is taken into CPDA anticoagulant, similar results can be obtained when the specimen is drawn directly into the specimen collection fluid without prior addition of anticoagulant.

EXAMPLE 2

A specimen collection fluid is made up comprising a sterile aqueous solution containing the following components by weight:

| | |
|---|---|
| Paraformaldehyde | 0.33 Molar |
| Dextrose (D-glucose) | 2.22 Molar |
| Adenosine tri phosphate | 0.036 Molar |
| Inosine | 0.075 Molar |
| Chloramphenicol | 0.012 Molar |
| Neomycin Sulphate | 0.0044 Molar |
| Chromium (III) Chloride | 0.019 Molar |
| Manganese Chloride | 0.025 Molar |
| Magnesium Chloride | 0.52 Molar |

The pH of the solution is adjusted to 7.4 and a heavy precipitate is formed. The solution is centrifuged at 1200 g to separate the precipitate from the supernatant. The supernatant is removed and filtered to remove any remaining particles.

$K_3$EDTA is added to make a final concentration of 0.34 Molar and the solution filtered again. 54 μl of the solution is placed in a 4.5 ml glass specimen collection tube. Blood drawn by venepuncture is immediately placed into the tube. The tubes contents are thoroughly mixed by inversion, to anticoagulate the fresh blood and initiate the stabilisation process. The tube is stored preferably at 4° C. and the contents allowed to warm up to room temperature before testing.

Figure 7A:
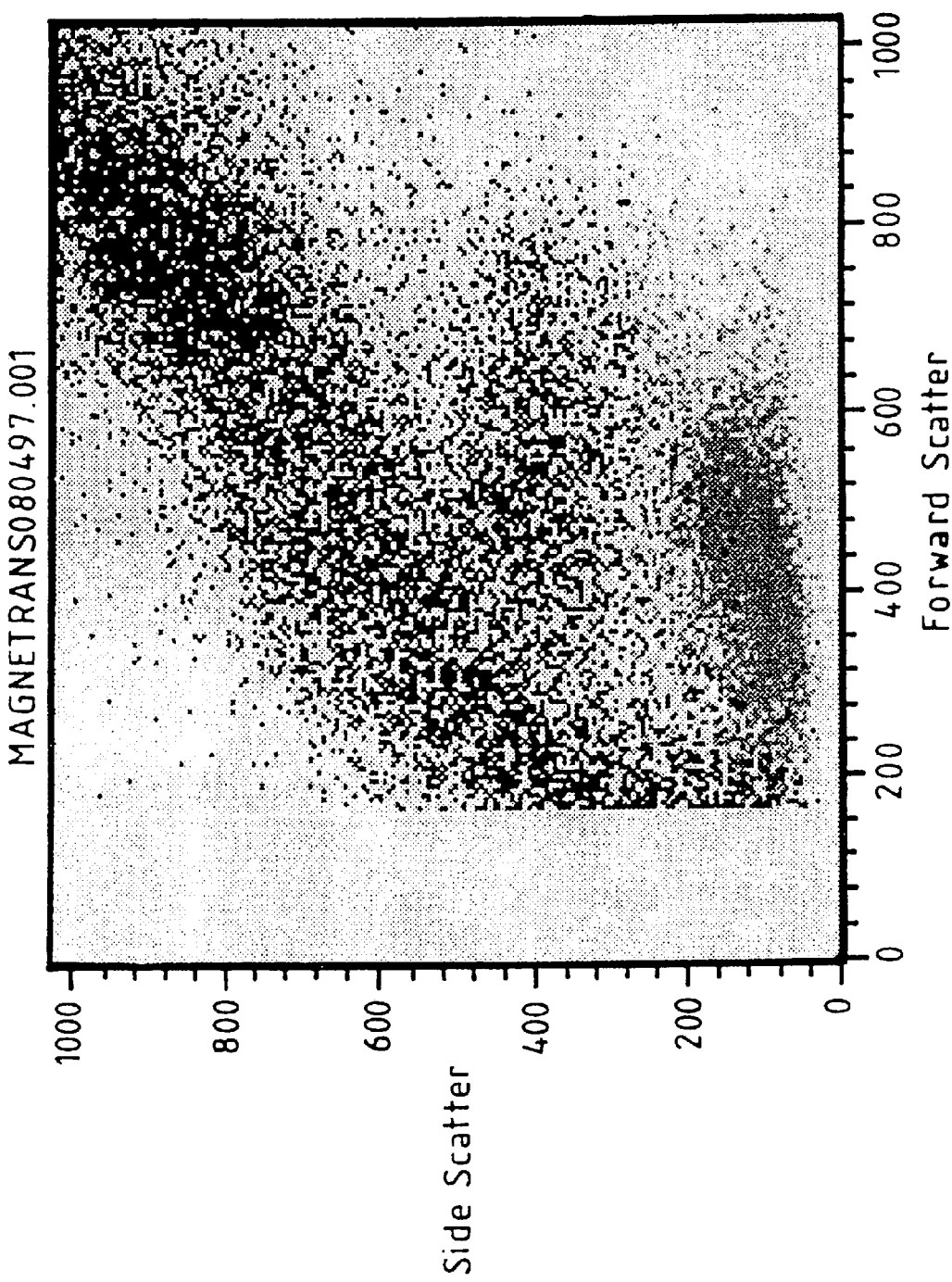

The specimen is tested on a Becton Dickinson flow cytometer after 5 days and compared to an unstabilised control. The results for CD45+ staining and side scatter are shown in FIGS. 5 and 6 (stabilised sample) and FIGS. 7 and 8 (control). It can be seen that whilst the stabilised specimen is comparatively unaffected, the agranulocytes have degraded and the amount of debris has markedly increased in the control specimen to the extent that the measurements are regarded as unreliable.

Whilst in the above example the specimen is anticoagulated by the $K_3$EDTA present in the stabilising fluid, similar results can be obtained by adding the stabilising fluid (without the $K_3$EDTA) directly into a previously anticoagulated specimen.

Figure 9:
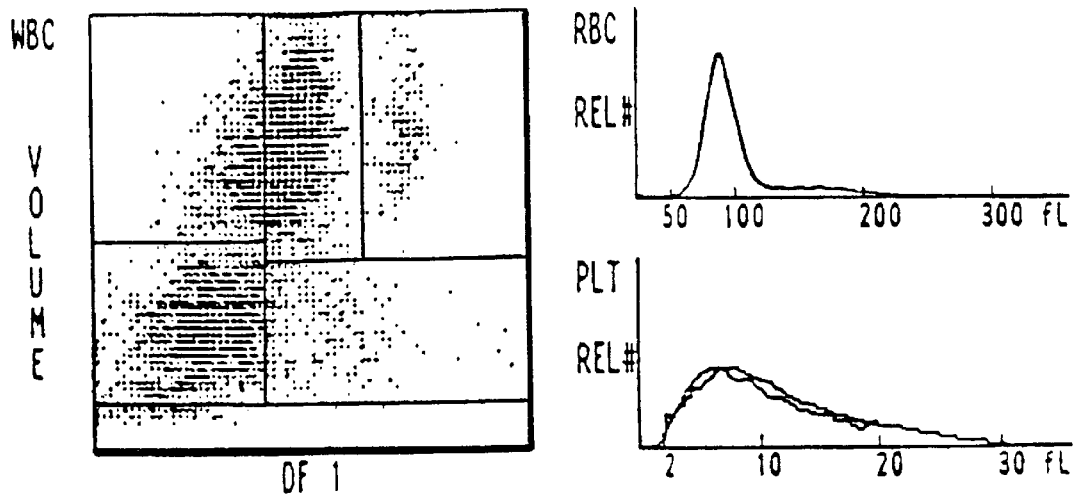
FIG. 9 is a full blood count profile of a blood specimen stored in contact with a specimen collection fluid of this invention.

Stabilised specimens in accordance with the invention can be tested on haematology analyzer machines such as a Coulter STKS without any rejection and give normal red cell and white cell counts. FIG. 9 shows a full blood count profile of a stabilised specimen 3 days post venepuncture. Tables 1 and 2 of FIG. 10 show respectively absolute values and percentage values for white cell differential over a 5 day period measured on a specimen stabilised in accordance with the procedure of Example 2.

It is also found that stabilised specimens in accordance with the invention have minimal haemolysis over a 7 day period.

Figure 11:
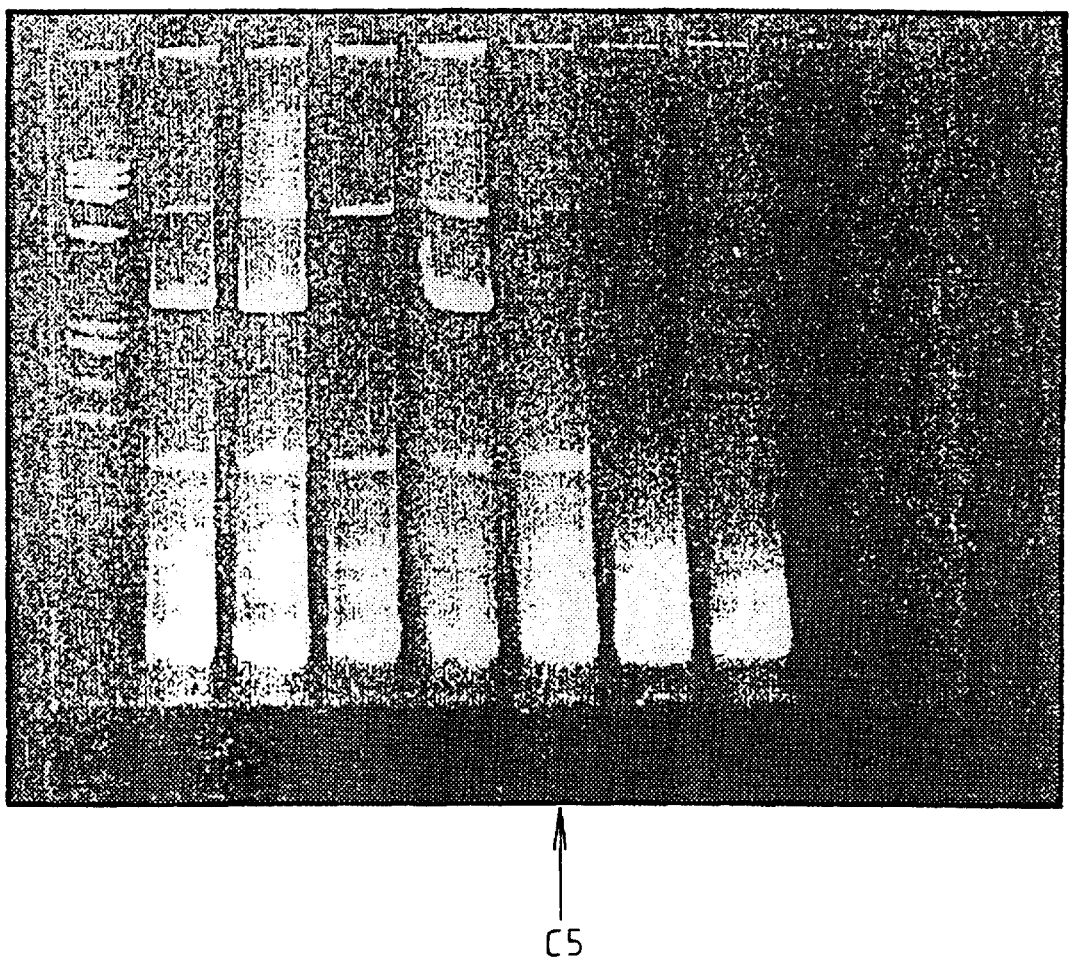
FIG. 11 is the results from an RT-PCR experiment on a whole blood sample stored in contact with a specimen collection fluid of this invention.

In FIG. 11, lane C5 shows the results of RT-PCR products from a 5 day old stabilised whole blood sample.

Typical values for RNA content in μg/ml over a 5 day period for unstabilised and stabilised samples are as follows:

| | |
|---|---|
| Unstabilised sample, day zero | 495 μg/ml RNA |
| Unstabilised sample, day five | 215 μg/ml RNA |
| Stabilised sample, day zero | 340 μg/ml RNA |
| Stabilised sample, day five | 240 μg/ml RNA |

The reader's attention is directed to all papers and documents which are filed concurrently with or previous to this specification in connection with this application and which are open to public inspection with this specification, and the contents of all such papers and comments are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

What is claimed is:

1. A method of collecting a whole blood specimen for haematological analysis, comprising contacting the whole blood specimen with a sterile aqueous whole blood specimen collection fluid comprising a buffer, an aliphatic aldehyde, at a concentration of 0.15M to 3.4M, and one or more heavy metal salts, at a total concentration of $0.2 \times 10^{-3}$M to 0.2M, the fluid having a pH of 6.8 to 8.0, wherein the specimen is taken directly into or transferred to a specimen collection container containing the specimen collection fluid.

2. A method according to claim 1, wherein the fluid further comprises an anticoagulant, at a concentration of 0.27M to 0.45M.

3. A method according to claim 1, wherein the ratio of the volume of the specimen to the volume of the specimen collection fluid is about 30:1 to 125:1.

* * * * *

UNITED STATES PATENT AND TRADEMARK OFFICE
CERTIFICATE OF CORRECTION

PATENT NO.     : 6,579,672 B1
DATED          : June 17, 2003
INVENTOR(S)    : Vivian Granger and David Barnett It is certified that error appears in the above-identified patent and that said Letters Patent is hereby corrected as shown below:

<u>Title page,</u>
Item [73], Assignee, "Northern General Hospital; and Central Sheffield University Hospitals NHS, Trust Royal Hallamshire Hospital" should read -- Sheffield Teaching Hospitals National Health Service Trust --.

Signed and Sealed this

Eighteenth Day of November, 2003

JAMES E. ROGAN
*Director of the United States Patent and Trademark Office*